: United States Patent (10) Patent No.: US 7,022,477 B2
Neriishi (45) Date of Patent: *Apr. 4, 2006

(54) DETECTION OF TARGET SUBSTANCES UTILIZING BIOCHEMICALLY SPECIFIC BINDING REACTION

(75) Inventor: Keiko Neriishi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 77 days.

This patent is subject to a terminal disclaimer.

(21) Appl. No.: 10/150,098

(22) Filed: May 20, 2002

(65) Prior Publication Data

US 2002/0186869 A1 Dec. 12, 2002

(30) Foreign Application Priority Data

May 18, 2001 (JP) ............................. 2001-150019
May 18, 2001 (JP) ............................. 2001-150020

(51) Int. Cl.
*C12Q 1/68* (2006.01)
*C12M 1/00* (2006.01)
*G01N 15/06* (2006.01)

(52) U.S. Cl. ...................... 435/6; 435/174; 435/283.1; 435/287.2; 422/68.1

(58) Field of Classification Search ................... 435/6, 435/174, 287.2, 288.4; 536/23.1; 422/68.1, 422/82.01
See application file for complete search history.

(56) References Cited

U.S. PATENT DOCUMENTS 5,055,681 A * 10/1991 Tsuchino et al. ........... 250/585
6,236,744 B1 * 5/2001 Some et al. ................ 382/132
6,255,660 B1 * 7/2001 Isoda et al. ................ 250/484.4
6,746,840 B1 * 6/2004 Neriishi ......................... 435/6
6,872,531 B1 * 3/2005 Hosoi ............................. 435/6

* cited by examiner

*Primary Examiner*—B J Forman
(74) *Attorney, Agent, or Firm*—Sughrue Mion, PLLC

(57) ABSTRACT

A composite material sheet which is composed of partitions two-dimensionally extending on a sheet plane to form on the sheet plane plural fine sections surrounded by the partitions and porous material portions each of which is placed in the fine section, or a simple porous sheet is employed for autoradiographic analysis of substances originating from living body or its analogues in combination with a stimulable phosphor sheet which is composed of a support and fine stimulable phosphor layers distributed on the support in such manner that each stimulable phosphor layer takes a position corresponding to each fine section of the composite material sheet or a position of the porous sheet in which probe molecules are spotted.

11 Claims, 4 Drawing Sheets

DETECTION OF TARGET SUBSTANCES UTILIZING BIOCHEMICALLY SPECIFIC BINDING REACTION

FIELD OF THE INVENTION

The present invention relates to a process for detecting substances originating from living body or analogues thereof according to biochemically specific binding reaction. In particular, the invention relates to an improved process utilizing a porous sheet and a stimulable phosphor sheet in combination.

BACKGROUND OF THE INVENTION

Recently, analytical elements such as a macro-array sheet and a micro-array sheet are widely utilized in gene analysis technology in the biological and medical fields. These analytical elements are used to analyze nucleic acids such as DNA and RNA, their fragments, and their duplicates such as PCR products. The analysis is performed by detecting the nucleic acids utilizing hybridization, which is one of biochemically specific binding reaction. The former macro-array sheet is made of porous sheet of polyamide resin or the like. For the analysis using the macro-array sheet, a large number of nucleic acid fragments (probe molecules) such as DNA fragments are first fixed to the porous sheet by entanglement. The binding reaction is carried out using (target) sample nucleic acid fragments labeled with radioisotope (RI). The latter micro-array is composed of solid carrier such as surface-treated slide glass plate. For the analysis using the micro-array sheet, the probe molecules are first fixed to the surface of the solid carrier. The binding reaction is carried out between the probe molecules and sample nucleic acid fragments labeled with fluorescent compound.

However, the names of macro-array sheet and micro-array sheet are not always employed distinctly to mean each of the above-described analytical elements.

The gene analysis utilizing a macro-array sheet is advantageous because it can be carried out using the conventional autoradiography.

The conventional procedures for detecting a nucleic acid such as DNA are generally conducted by the process comprising the following steps:

(1) preparing a number of single-stranded nucleic acid fragments (probe molecules: generally employed are those of which base sequences are already known); spotting in series an aqueous solution containing the fragments on a macro-array sheet using a spotter so that a large number of spots can be densely placed on the sheet to form a matrix composed of pores to which probe molecules are fixed by entanglement, whereby a large number of probe molecule spots in the form of dots are produced;

(2) bringing single-stranded sample nucleic acid fragments (to be analyzed) with a radioisotope label (RI, for instance, $^{32}P$ and $^{33}P$) contained in an aqueous solution into contact with the macro-array sheet (for instance, by immersing the macro-array sheet in an aqueous solution of the radioisotope-labeled sample nucleic acid fragments placed in a specific vessel) to fix target nucleic acid fragments to the macro-array sheet by hybridization with the probe molecules; namely, the target complementary nucleic acid fragments in the sample nucleic acid fragments are bound to the probe molecules in the spot by hybridization;

(3) removing unfixed radioisotope-labeled sample nucleic acid fragments from the macro-array sheet by washing;

(4) drying and placing the macro-array sheet on a radiographic film for detecting radiation coming from the radioisotope-labeled target nucleic acid fragments by autoradiography, whereby the binding information of the fixed target nucleic acid fragments (for instance, presence and amount of fixed fragments) are obtained; and (5) determining at least local base sequence information of the target nucleic acid fragments according to complementation principle, in the case that the base sequence of the probe molecules is previously known.

Thus, a large number of genes are simultaneously analyzed in their expression, mutation, and polymorphism, utilizing the above-described technology.

Recently, a radiation image recording and reproducing method utilizing a radiation image storage panel (which is also named "imaging plate" or "stimulable phosphor sheet") has been developed for performing autoradiography of radioisotope-labeled biological specimen and polymers originating from living body, in place of the conventional autoradiography using a radiographic film.

The radiation image recording and reproducing method utilizes stimulable phosphor (i.e., radiation image storage phosphor) which absorbs and stores radiation energy when it is exposed to radiation such as X rays, and thereafter produces emission in an amount proportional to the stored radiation energy when it is irradiated with electromagnetic wave (stimulating light) such as visible light or infrared rays, and is generally carried out by a procedure of the following steps:

applying to a stimulable phosphor sheet containing stimulable phosphor a radiation transmitted through or emitted by a target subject, whereby recording the radiation image in the phosphor sheet;

scanning sequentially the phosphor sheet with a stimulating light such as laser light, whereby the phosphor sheet sequentially produces stimulated emission;

photoelectrically detecting the stimulated emission to obtain a series of electric image signals (digital signals); and storing in an appropriate recording means the digital signals as such or after being subjected to various image processings for forming a visible image.

The autoradiography according to the above-described radiation image recording and reproducing method which utilizes a stimulable phosphor sheet is considered to be important autoradiogaphic technology, because it has various-advantageous features, for instance, it gives a radiation image with high sensitivity even if the amount of radiation coming from the radioisotope-labeled specimen is extremely small, and it gives an image information of digital data which is easily subjected to various image processing procedures and is easily stored.

The autoradiographic procedure utilizing the stimulable phosphor sheet for measuring radiation coming from radioisotope-labeled target molecules is already reported. For instance, Human Molecular Genetics, 1999, Vol. 8, No. 9, 1715–1722 describes that a target molecule can be detected by the steps of producing a large number of spots of DNA fragments (probe molecules) on a porous sheet, hybridizing radioisotope-labeled sample DNA fragments complementary to the probe molecules on the porous sheet, and carrying out the autoradiographic process by placing the porous sheet on a stimulable phosphor sheet.

The gene analysis utilizing a porous sheet such as a macro-array sheet enables to detect radioisotope-labeled target molecules with a high sensitivity when an autoradiographic process is performed utilizing the stimulable phosphor sheet. It has been noted by the inventor, however, that the spots of probe molecules are apt to spread on the porous sheet when a probe molecule solution is spotted on the porous sheet. Accordingly, it is difficult to satisfactorily increase a density of spots (i.e., number of spots per unit area) produced on the porous sheet. Moreover, if the area of spot of probe molecules spreads on the porous sheet, the area in which the radioisotope-labeled target molecules hybridized with the probe molecules also increases. In the increased spot area, the density of the hybridized target molecules decreases. Accordingly, the autoradiography produces a spot image at a less sensitivity, with large noise.

The noise of information is also produced by the fact that the target molecules are attached to the porous sheet not by hybridization.

SUMMARY OF THE INVENTION

The present invention has an object to provide a process for detecting substances originating from living body or analogues thereof with high sensitivity and low noise.

The present inventor has studied a process utilizing a porous sheet and a stimulable phosphor sheet for detecting substances originating from living body or analogues thereof. It has been noted that the detection utilizing a stimulable phosphor sheet sometimes shows detection errors which appear to be caused by the fact that the stimulable phosphor sheet absorbs not only the radiation energy emitted by the fixed radioactive target nucleic acid molecules but also radiation energy emitted by non-target radioactive nucleic acid molecules (namely, non-complementary radioactive nucleic acid molecules) which are inadvertently fixed to the porous sheet not by hybridization.

The inventor has further studied the analytical porous sheet and discovered that the spread of probe molecules on the porous sheet can be reduced by finely dividing the porous sheet by plural partitions extending on the sheet two-dimensionally. It is further noted that the partitions preferably do not transmit radiation.

In the above-mentioned structure of the porous sheet, the probe molecule solution spotted on the porous sheet spreads only within the divided porous area. If the divided porous area is produced on the sheet in a very small size, an increased number of spots of the probe molecules can be placed on the analytical sheet to increase efficiency of the analytical procedure.

The present invention provides a process for detecting complementary nucleic acid fragments which comprises the steps of:

preparing a composite material sheet which comprises partitions two-dimensionally extending on a sheet plane to form on the sheet plane plural fine sections surrounded by the partitions and porous material portions each of which is placed in the fine section, to each porous material portion of which a group of single-stranded probe nucleic acid fragments are attached;

bringing single-stranded sample nucleic acid fragments having a radioactive label in a liquid phase into contact with the prepared composite material sheet, whereby single-stranded target nucleic acid fragments in the sample nucleic acid fragments which are complementary to the group of the probe nucleic acid fragments are fixed by hybridization to the probe nucleic acid fragments;

removing unfixed sample nucleic acid fragments from the composite material sheet;

keeping the last-mentioned composite material sheet in contact with a stimulable phosphor sheet comprising a support and fine stimulable phosphor layers distributed on the support in such manner that each stimulable phosphor layer takes a position corresponding to each fine section of the composite material sheet, where the stimulable phosphor layers absorb and store radiation energy of the radioactive label coming from the fixed nucleic acid fragments;

irradiating the stimulable phosphor sheet with a stimulating light, whereby the stimulable phosphor layers in which the radiation energy is stored release stimulated emissions;

detecting the stimulated emissions photoelectrically to obtain a series of electric signals; and processing the electric signals to detect areas in which the complementary nucleic acid fragments are fixed.

The invention further resides in a kit comprising a composite material sheet which comprises partitions two-dimensionally extending on a sheet plane to form on the sheet plane plural fine sections surrounded by the partitions and porous material portions each of which is placed in the fine section, and a stimulable phosphor sheet which comprises a support and fine stimulable phosphor layers distributed on the support in such manner that each stimulable phosphor layer takes a position corresponding to each fine section of the composite material sheet.

The invention furthermore resides in a process for detecting complementary nucleic acid fragments which comprises the steps of:

preparing a porous material sheet which has at predetermined positions plural dots comprising a group of single-stranded probe nucleic acid fragments;

bringing single-stranded sample nucleic acid fragments having a radioactive label in a liquid phase into contact with the prepared porous material sheet, whereby single-stranded target nucleic acid fragments in the sample nucleic acid fragments which are complementary to the group of the probe nucleic acid fragments are fixed by hybridization to the probe nucleic acid fragments;

removing unfixed sample nucleic acid fragments from the composite material sheet;

keeping the last-mentioned porous material sheet in contact with a stimulable phosphor sheet comprising a support and fine stimulable phosphor layers distributed on the support in such manner that each stimulable phosphor layer takes a position corresponding to the position of each dot of the probe nucleic acid fragments, whereby the stimulable phosphor layers absorb and store radiation energy of the radioactive label coming from the fixed nucleic acid fragments;

irradiating the stimulable phosphor sheet with a stimulating light, whereby the stimulable phosphor layers in which the radiation energy is stored release stimulated emissions;

detecting the stimulated emissions photoelectrically to obtain a series of electric signals; and processing the electric signals to detect dots in which the complementary nucleic acid fragments are fixed.

The invention furthermore resides in a kit comprising a porous material sheet which has at predetermined positions plural dots comprising a group of single-stranded probe nucleic acid fragments, and a stimulable phosphor sheet which comprises a support and fine stimulable phosphor layers distributed on the support in such manner that each stimulable phosphor layer takes a position corresponding to each dot on the porous material sheet.

The substances originating from living body or analogues thereof to be detected according to the detection process of the invention can be substances directly taken from living body by extraction or isolation, substances obtained by subjecting the above-mentioned substances to chemical treatment or modification, or substances duplicated from these substances, for instance, using PCR technology. Representative examples of the substances include nucleic acids such as polynucleotides (e.g., DNA and RNA) and peptide nucleic acid (PNA), their fragments, antigens, antibodies, tumor markers, enzymes, abzymes, hormones, and other proteins.

The biochemically specific binding reactions utilizable in the invention can be hybridization occurring according to complementation of base sequence, an immunological specific binding reaction such as antigen-antibody reaction, and a protein specific binding reaction occurring between proteins having specific steric structures.

The composite material sheet of the invention preferably has one or more of the following features.

(1) The difference between the mean density of material of the partitions and the mean density of the porous material portions is not less than 0.1 g/cm$^3$, preferably not less than 0.5 g/cm$^3$, more preferably not less than 1.0 g/cm$^3$.

(2) The mean density of material of the partitions is in the range of 1 to 20 g/cm$^3$, preferably 2 to 10 g/cm$^3$.

(3) The mean density of the porous material portions is in the range of 0.1 to 0.5 g/cm$^3$.

(4) The partitions are made of metal, plastic material, or ceramics, preferably nickel metal or nickel alloy.

(5) The porous material portions are made of porous organic polymer material, preferably porous polyamide or porous cellulose derivatives.

(6) The fine sections having the porous material portion therein have an opening whose mean area is smaller than 5 mm$^2$, preferably smaller than 1 mm$^2$, more preferably smaller than 0.1 mm$^2$, and larger than 0.001 mm$^2$, preferably larger than 0.01 mm$^2$.

(7) The fine sections having the porous material portion therein are produced in numbers per cm$^2$ (density) of not less than 10, preferably not less than 100, more preferably not less than 1,000, and not more than 100,000, more preferably not more than 10,000.

The stimulable phosphor sheet of the invention preferably has stimulable phosphor layers which are are separated from each other by partitions having a mean density of not lower than 0.6 g/cm$^3$.

DETAILED DESCRIPTION OF THE INVENTION

The composite material sheet of the invention comprises partitions extending two-dimensionally on the sheet to divide the sheet to give a large number of fine sections and a corresponding large number of porous material portions placed in the fine sections.

The structure of the composite material sheet is explained by referring to the attached drawings.

Figure 1:
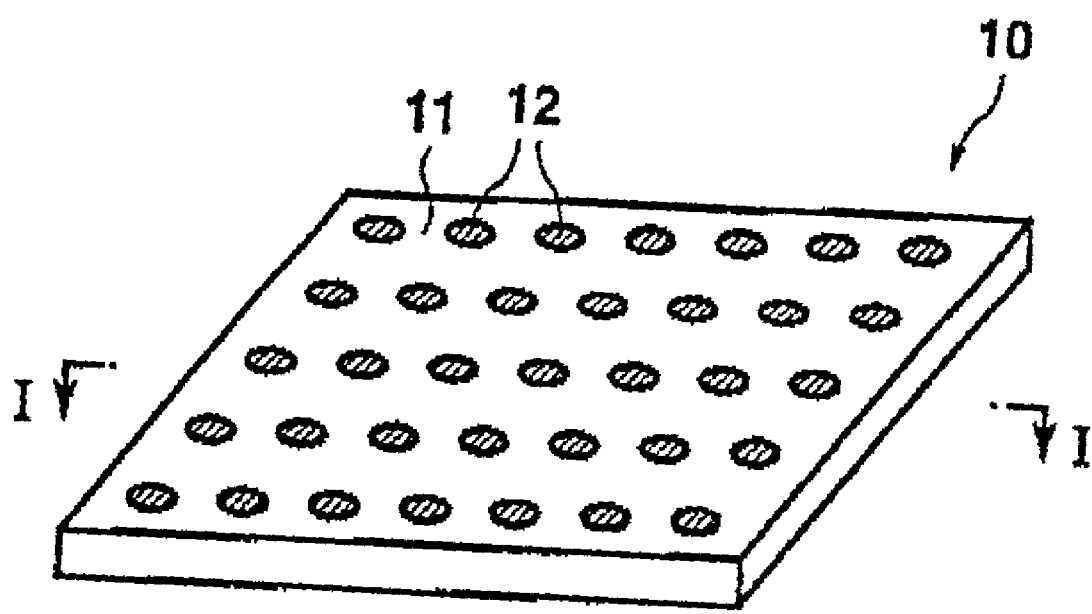
FIG. 1 is a schematic view of a composite material sheet according to the invention.
Figure 2:
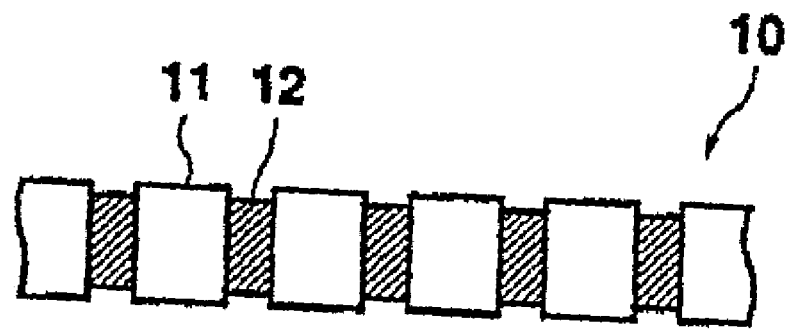
FIG. 2 is an enlarged view of the section taken out along I—I line of FIG. 1.

FIG. 1 is a schematic view of the composite material sheet according to the invention, and FIG. 2 is an enlarged view of the section taken out along I—I line of FIG. 1.

In FIGS. 1 and 2, the composite material sheet is composed of partitions 11 giving a large number of though-holes and porous material portions (i.e., porous structure portions: shadow area) 12 enclosed with the partitions 11. The porous material portions 12 are placed within the small through-holes. The opening of the through-hole generally has an area of smaller than 5 mm$^2$, preferably smaller than 1 mm$^2$, more preferably smaller than 0.1 mm$^2$, and larger than 0.001 mm$^2$, preferably larger than 0.01 mm$^2$.

It is preferred that at least one of the upper surface and lower surface of the porous material portion 12 is retracted from the upper surface and lower surface of the adjoining partitions. Such structure of the porous material portion enables to receive spotting of a probe solution and prohibits overflow of the spotted solution onto the adjoining porous material portions.

The fine sections in each of which the porous material portion is placed are generally produced in numbers per cm$^2$ (i.e., density) of not less than 10, preferably not less than 100, more preferably not less than 1,000, but not more than 100,000, more preferably not more than 10,000. The fine sections are not always provided at equal spaces. Plural groups of fine sections are separately located on the sheet.

The partitions 11 have a mean density of not less than 0.6 g/cm$^3$, preferably in the range of 1 to 20 g/cm$^3$, more preferably in the range of 2 to 10 g/cm$^3$ so that the partitions can efficiently shield transmission of radiation such as electron rays. It is known that the distance of transmission of radiation is inversely proportional to the density of material. Therefore, if the radioisotope (RI) is ordinary one such as $^{32}P$, $^{33}P$, $^{35}S$, or $^{14}C$, the partition having such mean density can effectively shield transmission of radiation therethrough, and protects a reproduced radiation image from lowering of resolution.

Examples of material of the partition having such mean density include metal such as nickel or nickel alloy, plastic material such as polyamide resin, aramid resin, polyethylene terephthalate resin, polyolefin resin (e.g., polyethylene resin or polypropylene resin); and ceramics such as alumina, zirconia, magnesia, and quartz.

The porous material portions 12 of the composite material sheet to which probe molecules such as nucleic acids, its fragments, synthesized oligonucleotides are fixed have a mean density of not higher than 1.0 g/cm$^3$, preferably not higher than 0.5 g/cm$^3$, but not lower than 0.1 g/cm$^3$, under the condition that the mean density of the porous material portions is lower than the mean density of material of the partitions.

The porous material portions generally occupy 10 to 90 volume % of the composite material sheet, and a mean pore size generally is in the range of 0.1 to 50 μm.

The porous material portions are preferably produced from organic polymer material such as cellulose derivative (e.g., cellulose acetate or nitrocellulose), polyamide (nylon, e.g., 6-nylon or 6,6-nylon), fluoropolymer (e.g., polytetrafluoroethylene or polyvinylidene fluoride), polyvinyl chloride, polycarbonate, polysulfone, or polyether sulfone or inorganic material such as ceramics. These materials can be employed in combination, if desired.

The arrangement and shapes of the openings of the porous material portions 12 are not limited to the grid arrangement and round openings illustrated in FIG. 1. Other arrangements and shapes can be adopted.

Figure 3:
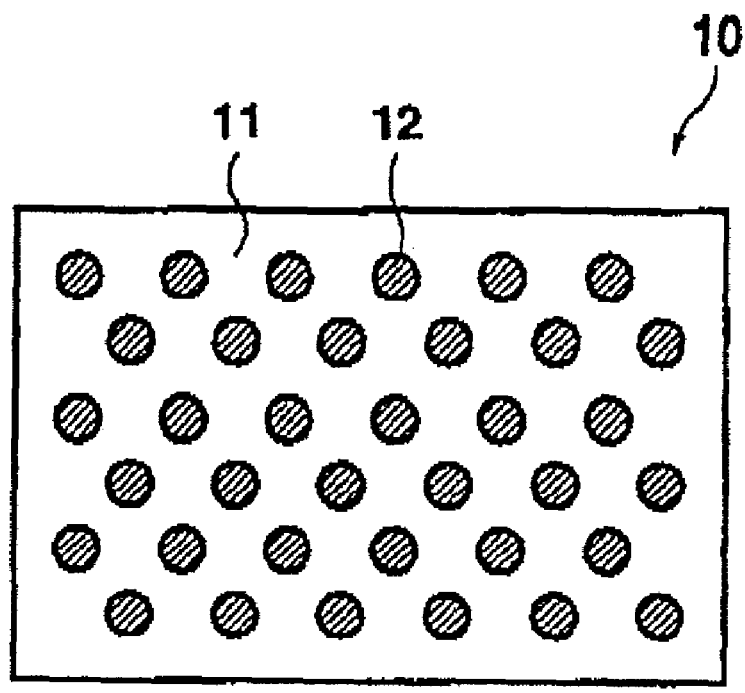
FIG. 3 is a plane view showing a variation of pattern of arrangement of the porous material portions.

FIG. 3 is a plane view showing a variation of pattern of the arrangement of porous material portions. In FIG. 3, a group of the porous material portions are composed of plural rows of porous material portions which are arranged with sequential shift of the positions of the porous material portions.

Figure 4:
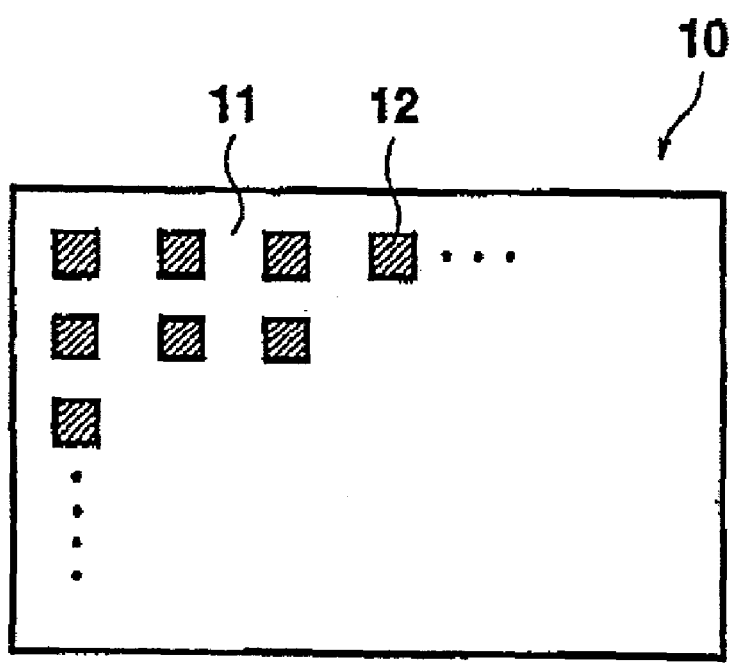
FIG. 4 is a plane view showing the porous material portions which have openings of a different shape.
Figure 5:
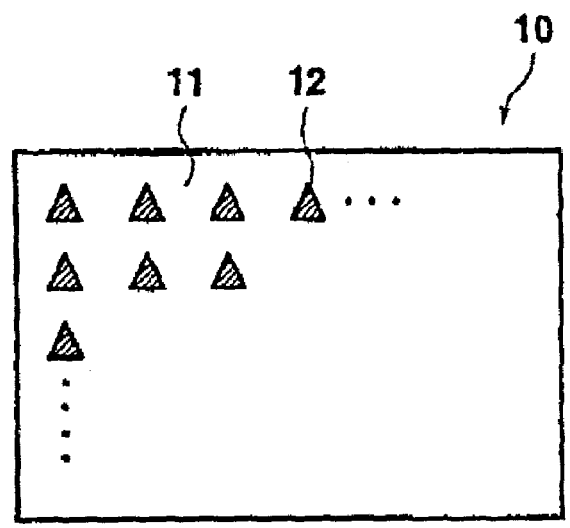
FIG. 5 is a plane view showing the porous material portions which have openings of a different shape.

Both of FIG. 4 and FIG. 5 are plane views showing variations of the shape of opening of the porous material portion. In FIG. 4, the opening of the porous material portion 12 takes a shape of square, while the opening of the porous material portion 12 takes a shape of triangle in FIG. 5.

Alternatively, the porous material portions are arranged at random on the composite material sheet, and the shape of opening can be oval or polygonal such as hexagonal.

The composite material sheet of the invention can be prepared by the following process.

First, a substrate having a desired partition pattern is produced using the aforementioned partition material. For instance, if the partition material is metal, the metal is electrocast on an appropriate mould to produce a substrate having a large number of openings. If the partition material is plastic resin, the plastic resin is dissolved in a solvent to give a resin solution and the resin solution is casted and dried to give a resin sheet. The resin sheet is etched by lithography such as dry etching or laser processing utilizing LIGA process or excimer laser, to give the desired substrate having a large number of openings. If the partition material is ceramics material, a slurry of ceramics material are molded and pressed to give a ceramic sheet. The ceramic sheet is then etched by laser or other means so that the ceramic sheet can have a large number of openings.

Separately, the material for the porous material portion is dissolved or dispersed in an appropriate solvent to give a solution or dispersion. The solution or dispersion is then placed in each opening of the substrate produced above, and dried to give a porous material portion in each opening. In the case using polyamide which shrinks in contact with water, a non-aqueous polyamide solution is first placed in the openings and dried to produce membrane and subsequently thus produced sheet is immersed in an aqueous medium to produce micro-pores in the polyamide mane in each opening. In the case using ceramics, ceramic particles having micro-pores are dispersed, placed in the openings, and dried.

Alternatively, an independently prepared porous material sheet can be placed on the substrate having a large number of openings under pressure so that portions of the porous material sheet are pushed into the openings of the substrate.

Thus, a composite material sheet comprising a substrate having a large number of openings and porous material portions placed in the openings such as that illustrated in FIGS. 1 and 2 is prepared.

In the detection process of the invention, a simple porous sheet can be employed in place of the composite material sheet. The simple porous sheet can be the one which is employed as a macro-array sheet in the known method for detecting substances originating from living body or its analogues. The simple porous sheet can be prepared from organic polymer material such as cellulose derivative (e.g., cellulose acetate or nitrocellulose), polyamide (nylon, e.g., 6-nylon or 6,6-nylon), fluoropolymer (e.g., polytetrafluoroethylene or polyvinylidene fluoride), polyvinyl chloride, polycarbonate, polysulfone, or polyether sulfone or inorganic material such as ceramics. These materials can be employed in combination, if desired.

The probe molecules to be fixed on the composite material sheet can be polynucleotides or oligonucleotides which are conventionally employed for the conventional macro-array sheet. For instance, cDNA (complementary DNA synthesized using mRNA as template), a portion of cDNA, polynucleotide prepared by multiplation utilizing PCR method such as EST (PCR product), and synthesized oligonucleotide can be mentioned. Alternatively, an artificial nucleic acid prepared from DNA by changing the phosphodiester bondings to peptide bondings, namely, PNA, or its derivative. Otherwise, proteins such as antigen or antibodies which can pertain in immunological specific binding reaction can be employed as probe molecules.

Examples of the combinations between the probe molecule and target molecule include DNA (or DNA fragment, or oligo DNA) and DNA, DNA and RNA, PNA and DNA (or RNA), PNA and PNA, antigen and antibody, and abidine and biotin.

The process for detecting substances originating from living body, their fragments, or their duplicate products is generally carried out by the following steps:

preparing the composite material sheet to each porous material portion of which a group of probe molecules are attached, or the porous material sheet to which a group of probe molecules are attached in the predetermined positions;

bringing sample molecules having a radioactive label in the presence of water into contact with the prepared composite material sheet, whereby target molecule (contained in the sample molecules) complementary to the probe molecules in the sample molecules are fixed by hybridization to the probe molecules;

removing unfixed sample molecules from the composite material sheet;

keeping the last-mentioned composite material sheet in contact with a stimulable phosphor sheet so that the stimulable phosphor sheet can absorb and store radiation energy of the radioactive label coming from the fixed target molecules—autoradiography;

irradiating the stimulable phosphor sheet with a stimulating light, whereby the stimulable phosphor sheet releases stimulated emissions from the areas in which the radiation energy is stored;

detecting the stimulated emissions photoelectrically to obtain a series of electric signals; and processing the electric signals to detect the area in which the complementary target molecules are fixed.

The stimulable phosphor sheet is described in various publications, and the autoradiography utilizing the stimulable phosphor sheet is also described in various publications and is practically employed.

The stimulable phosphor sheet of the invention comprises a support sheet and finely divided stimulable phosphor layers which are distributed on the support in such manner that each stimulable phosphor layer takes a position corresponding to each fine section of the composite material sheet or to each position in which a sample molecule solution is to be spotted.

Figure 6:
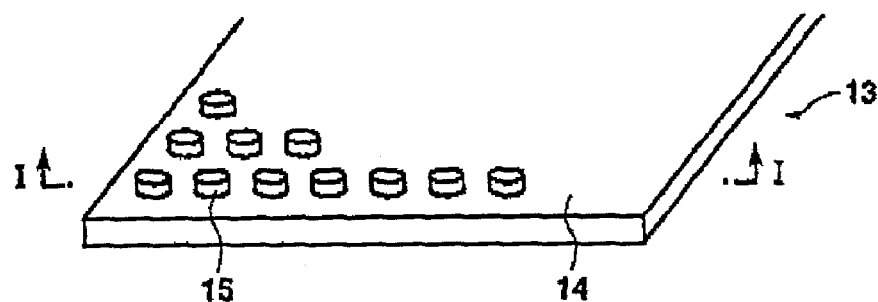
FIG. 6 is a schematic view of a stimulable phosphor sheet employable in the invention.
Figure 7:
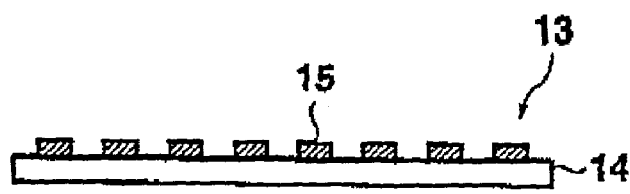
FIG. 7 is an enlarged view of the section taken out along I—I line of FIG. 6.

In FIG. 6 and FIG. 7, a stimulable phosphor sheet of the invention is illustrated, respectively, by schematic view and section view. In FIGS. 6 and 7, the stimulable phosphor sheet 13 is composed of a support 14 and plural stimulable phosphor layers 15 in the form of dots which are produced on the support 15 separately.

Figure 8:
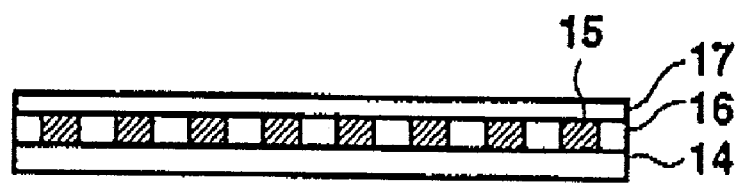
FIG. 8 is a partial section of another stimulable phosphor sheet employable in the invention.

The stimulable phosphor sheet of the invention preferably takes a structure of FIG. 8 in which the plural stimulable phosphor layers in the form of dots are isolated from each other by high density partitions 16 (for instance, having a density of not less than 0.6 g/cm$^3$) so that radiation energy in one dot does not penetrate the surrounding partitions. Moreover, a protective layer such as a cover sheet 17 is placed on the stimulable phosphor layers. It is noted that the stimulable phosphor layers may be placed on the support uniformly or locally.

As the stimulable phosphor, a phosphor giving a stimulated emission of a wavelength in the region of 300 to 500 nm when it is irradiated with stimulating rays of a wavelength in the region of 400 to 900 nm is preferably employed. In Japanese Patent Provisional Publications No. 2-193100 and No. 4-310900, some examples of the stimulable phosphors are described in detail. Examples of the preferred stimulable phosphors include divalent europium or cerium activated alkaline earth metal halide phosphors (e.g., BaFBr:Eu, BaF(BrI):Eu), and cerium activated oxyhalide phosphors.

The autoradiography is generally performed by placing a stimulable phosphor sheet on the composite material sheet having complementary radioisotope-labeled target molecules by hybridization, at a temperature in the range of 0 to 30° C., for one hour to 120 hours.

Figure 10:
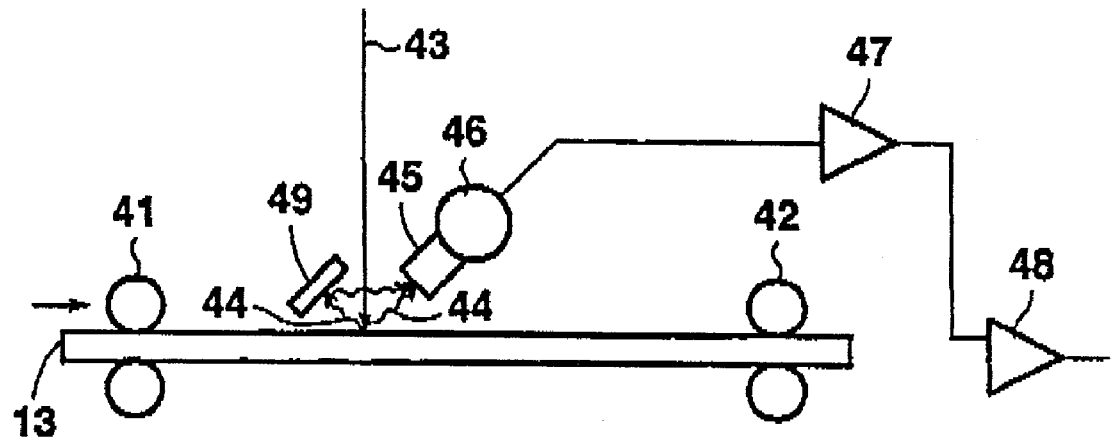
FIG. 10 illustrates an apparatus for reproducing a radiation image from a stimulable phosphor sheet which has been subjected to autoradiographic procedure.

The typical radiation image reproducing procedure is illustrated in FIG. 10.

In FIG. 10, a radiation image storage panel 13 is transferred in the direction of arrow, by means of a pair of rollers 31. On the storage panel 13 is applied a stimulating light 33. A stimulated emission 34 is directly detected by a light detecting means 35 or indirectly detected after reflection on a mirror 39. In the photoelectric conversion means 36, the stimulated emission 34 is converted into a series of electric signals, which are then transmitted to a multiplier 37 and further processed in a processor 38.

In the processor 38, a series of electric signals supplied from the multiplier 37 are subjected to appropriate processing such as addition or deduction depending on the nature of the desired radiation image or the characteristics of the employed stimulable phosphor sheet. Thus processed electric signals are then output as a set of image signals.

The set of image signals are subsequently reproduced on a display (e.g., CRT), recorded on an appropriate storage device such as photographic film, optical disc, or magnetic disc.

The invention is further described by the following non-limitative examples.

EXAMPLE 1

(1) Production of Substrate Having Fine Through-holes

A substrate having a large number of small through-holes were produced by electrocasting nickel metal on a mould. The produced substrate had a size of 40 mm×60 mm, a thickness of 0.2 mm, 2,400 through-holes, and a density (number per cm$^2$) of through-holes of 100/cm$^2$. The through-hole has an round opening of 0.07 mm$^2$. A mean density of the substrate (corresponding to mean density of the partitions) was 8.8 g/cm$^3$.

(2) Production of Porous Material Portions

To a mixture of 83 wt. % of formic acid and 2 wt. % of water was added 15 wt. % of nylon 6, and the resulting mixture was well mixed at room temperature for 3 hours. The mixture was further mixed at 50° C. for one hour to give a polymer solution. The polymer solution was then cooled to reach room temperature. The cooled polymer solution was poured into the though-holes of the substrate. The poured solution was dried to give a membrane in each through-hole. The substrate having a membrane in each through-hole was immersed into an aqueous formic acid solution (formic acid concentration: 20 wt. %), so that a large number of micro-pores were produced in each membrane. Thus, a composite material sheet composed of a nickel substrate having partitions and porous nylon-6 membrane portions (such as that illustrated in FIGS. 1 and 2) was produced.

(3) Evaluation of Autoradiographic Process

To each porous nylon-6 membrane portion of the composite material sheet were attached single-stranded nucleic acid fragments (probe molecules) according to the well known method. The composite material sheet was then immersed in a solution of separately prepared radioactively labeled single-stranded nucleic acids (target molecules) complementary to the probe molecules, for carrying out hybridization.

Figure 9:
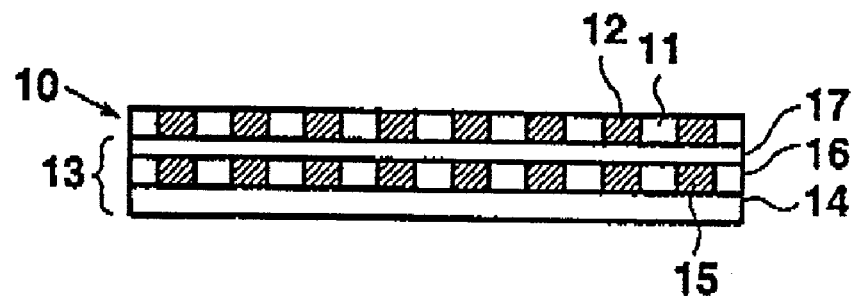
FIG. 9 illustrate a section of a combined structure of a composite porous sheet and a stimulable phosphor sheet.

The composite material sheet was taken out of the solution, washed with water, and dried. The composite material sheet was then placed on a stimulable phosphor sheet having a support sheet, plural fine stimulable phosphor layers in the form of dots on the support, and a cover sheet (such as that illustrated in FIG. 8) for performing autoradiography at room temperature. In the autoradiographic procedure, the composite material sheet was placed on the stimulable phosphor sheet in such manner that the positions of the porous material portions having fixed target molecules therein face the stimulable phosphor layers, in the manner described in FIG. 9.

The stimulable phosphor sheet subjected to autoradiography was then subjected to radiation image storing and reproducing procedure, using an apparatus such as that illustrated in FIG. 10. There was obtained a radiation image indicating the positions of porous membrane areas in which the radioactively-labeled target molecules were placed by hybridization with the probe molecules, with high sensitivity and high resolution.

EXAMPLE 2

(1) Production of Substrate Having Fine Through-holes

A substrate having a large number of small through-holes were produced in the same manner as in (1) of Example 1.

(2) Production of Porous Material Portions

To a mixture of 54 wt. % of methylene chloride and 35 wt. % of methanol was added 7.5 wt. % of cellulose acetate (percentage of acetylation: 60%), and the resulting mixture was well mixed at room temperature for 3 hours. The mixture was further mixed at 50° C. for one hour to give a polymer solution. The polymer solution was then cooled to reach room temperature. The cooled polymer solution was poured into the through-holes of the substrate. The poured solution was dried for 5 minutes without applying air to the solution to give a membrane in each through-hole. The substrate having a membrane in each through-hole was further dried for 20 minutes at 25° C. 60% RH, with applying air slowly, to produce micro-pores in the membrane. Thus, a composite material sheet composed of a nickel substrate having partitions and porous cellulose acetate membrane portions (such as that illustrated in FIGS. 1 and 2) was produced.

(3) Evaluation of Autoradiographic Process

To each cellulose acetate porous membrane portion of the composite material sheet were attached single-stranded nucleic acid fragments (probe molecules) according to the well know method. The composite material sheet was then immersed in a solution of separately prepared radioactively labeled single-stranded nucleic acids (target molecules) complementary to the probe molecules, for carrying out hybridization.

The composite material sheet was taken out of the solution, washed with water, and dried. The composite material sheet was then placed on a stimulable phosphor sheet having a support sheet, plural fine stimulable phosphor layers in the form of dots on the support, and a cover sheet (such as that illustrated in FIG. 8) for performing autoradiography at room temperature. In the autoradiogaphic procedure, the composite material sheet was placed on the stimulable phosphor sheet in such manner that the positions of the porous material portions having fixed target molecules therein face the stimulable phosphor layer, in the manner described in FIG. 9.

The stimulable phosphor sheet subjected to autoradiography was then subjected to radiation image storing and reproducing procedure, using an apparatus such as that illustrated in FIG. 10. There was obtained a radiation image indicating the positions of porous membrane areas in which the radioactively-labeled target molecules were placed by hybridization with the probe molecules, with high sensitivity and high resolution.

EXAMPLE 3

To a commercially available porous nylon-6 membrane sheet were attached single-stranded nucleic acid fragments (probe molecules) in the predetermined positions according to the well known method. The membrane sheet was then immersed in a solution of separately prepared radioactively labeled single-stranded nucleic acids (target molecules). complementary to the probe molecules, for carrying out hybridization.

The membrane sheet was taken out of the solution, washed with water, and dried. The membrane sheet was then placed on a stimulable phosphor sheet having a support sheet, plural fine stimulable phosphor layers in the form of dots on the support, and a cover sheet (such as that illustrated in FIG. 8) for performing autoradiography at room temperature. In the autoradiographic procedure, the membrane sheet was placed on the stimulable phosphor sheet in such that the positions of the fixed probe molecules face the stimulable phosphor layers.

The stimulable phosphor sheet subjected to autoradiography was then subjected to radiation image storing and reproducing procedure, using an apparatus such as that illustrated in FIG. 10. There was obtained a radiation image indicating the positions of porous membrane areas in which the radioactively-labeled target molecules were placed by hybridization with the probe molecules, with high sensitivity and high resolution.

EXAMPLE 4

A porous material sheet was prepared using cellulose acetate (degree of acetylation: 60%).

To the cellulose acetate porous sheet were attached single-stranded nucleic acid fragments (probe molecules) in the predetermined positions according to the well known method. The porous sheet was then immersed in a solution of separately prepared radioactively labeled single-stranded nucleic acids (target molecules) complementary to the probe molecules, for carrying out hybridization.

The porous sheet was taken out of the solution, washed with water, and dried. The porous sheet was then placed on a stimulable phosphor sheet having a support sheet, plural fine stimulable phosphor layers in the form of dots on the support, and a cover sheet (such as that illustrated in FIG. 8) for performing autoradiography at room temperature. In the autoradiographic procedure, the porous sheet was placed on the stimulable phosphor sheet in such manner that the positions of the fixed probe molecules face the stimulable phosphor layers.

The stimulable phosphor sheet subjected to autoradiography was then subjected to radiation image storing and reproducing procedure, using an apparatus such as that illustrated in FIG. 10. There was obtained a radiation image indicating the positions of areas in which the radioactively-labeled target molecules were placed by hybridization with the probe molecules, with high sensitivity and high resolution.

What is claimed is:

1. A process for detecting complementary nucleic acid fragments which comprises the steps of:
    preparing a composite material sheet, wherein said composite material sheet comprises partitions two-dimensionally extending on a sheet plane to form 10 to 10,000 per $cm^2$ fine sections on the sheet plane, and a porous material portion placed in each fine section, wherein a group of single-stranded probe nucleic acid fragments are attached to each porous material portion;
    bringing radioactively labeled single-stranded sample nucleic acid fragments in a liquid phase, into contact with the prepared composite material sheet, whereby single-stranded target nucleic acid fragments amoung the sample nucleic acid fragments are fixed by hybridization to probe nucleic acid fragments;
    removing unfixed sample nucleic acid fragments from the composite material sheet;
    placing the composite material sheet having target nucleic acid fragments fixed by hybridization in contact with a stimulable phosphor sheet, wherein the stimulable phosphor sheet comprises a support and fine stimulable phosphor layers distributed on the support in such manner that each stimulable phosphor layer takes a position corresponding to each fine section of the composite material sheet, whereby the stimulable phosphor layers absorb and store radiation energy of the radioactive label coming from the fixed nucleic acid fragments;
    irradiating the stimulable phosphor sheet with a stimulating light, whereby the stimulable phosphor layers storing the radiation energy release stimulated emissions;
    detecting the stimulated emissions photoelectrically to obtain a series of electric signals; and
    processing the electric signals to detect areas in which the target nucleic acid fragments are fixed.

2. The process of claim 1, wherein the partitions of the composite material sheet are made of material having a mean density of not lower than 0.6 g/cm$^3$ and the porous material portions have a mean density of not higher than 1.0 g/cm$^3$, provided that the mean density of material of the partitions is higher than the mean density of the material of the porous material portions.

3. The process of claim 2, wherein the partitions are made of metal, plastic material, or ceramics.

4. The process of claim 1, wherein the porous material portions of the composite material sheet are made of porous organic polymer material.

5. The process of claim 1, wherein the fine sections of the composite material sheet have an opening whose mean area is in the range of 0.001 to 5 mm$^2$.

6. The process of claim 1, wherein at least one of an upper and a lower surface of the porous material portions retracts from an upper or a lower surface of adjoining partitions on the sheet plane.

7. The process of claim 1, wherein the single-stranded probe nucleic acid fragments are derived from oligonucleotides or polynucleotides.

8. The process of claim 1, wherein the mean density of the porous material portions of the composite material sheet is in the range of 0.1 to 0.5 g/cm$^3$.

9. The process of claim 1, wherein the mean density of material of the partitions of the composite material sheet is in the range of 1 to 20 g/cm$^3$.

10. The process of claim 1, wherein the stimulable phosphor layers of the stimulable phosphor sheet are separated from each other by partitions having a mean density of not lower than 0.6 g/cm$^3$.

11. A process for detecting complementary nucleic acid fragments which comprises the steps of:

preparing a composite material sheet, wherein said composite material sheet comprises partitions two-dimensionally extending on a sheet plane to form plural fine sections, on the sheet plane, having an opening with a mean area in the range of 0.001 to 5 mm$^2$, and a porous material portion placed in each fine section, wherein a group of single-stranded probe nucleic acid fragments are attached to each porous material portion;

bringing radioactively labeled single-stranded sample nucleic acid fragments in a liquid phase, into contact with the prepared composite material sheet, whereby single-stranded target nucleic acid fragments among the sample nucleic acid fragments are fixed by hybridization to probe nucleic acid fragments;

removing unfixed sample nucleic acid fragments from the composite material sheet;

placing the composite material sheet having target nucleic acid fragments fixed by hybridization in contact with a stimulable phosphor sheet, wherein said stimulable phosphor sheet comprises a support and fine stimulable phosphor layers distributed on the support in such manner that each stimulable phosphor layer takes a position corresponding to each fine section of the composite material sheet, whereby the stimulable phosphor layers absorb and store radiation energy of the radioactive label coming from the fixed nucleic acid fragments;

irradiating the stimulable phosphor sheet with a stimulating light, whereby the stimulable phosphor layers storing the radiation energy release stimulated emissions;

detecting the stimulated emissions photoelectrically to obtain a series of electric signals; and processing the electric signals to detect areas in which the target nucleic acid fragments are fixed.

\* \* \* \* \*